United States Patent [19]
Hon

[11] Patent Number: 5,671,749
[45] Date of Patent: Sep. 30, 1997

[54] METHOD FOR THE DIAGNOSIS OF PRETERM BIRTH

[76] Inventor: Edward H. Hon, 11 Bradbury Hills Rd., Bradbury, Calif. 91010

[21] Appl. No.: 436,632

[22] Filed: May 8, 1995

Related U.S. Application Data

[63] Continuation-in-part of Ser. No. 85,547, Jun. 30, 1993, Pat. No. 5,497,778.

[51] Int. Cl.$^6$ ............................................. A61B 5/0205
[52] U.S. Cl. ........................ 128/670; 128/691; 128/775; 128/672; 607/902
[58] Field of Search .................................. 128/670, 672, 128/691, 775; 607/902

[56] References Cited

U.S. PATENT DOCUMENTS

| | | | |
|---|---|---|---|
| 4,967,761 | 11/1990 | Nathanielsz | 128/775 |
| 4,993,422 | 2/1991 | Hon et al. | 128/672 |
| 5,069,218 | 12/1991 | Ikeda | 128/670 |
| 5,373,852 | 12/1994 | Harrison et al. | 128/775 |

FOREIGN PATENT DOCUMENTS

| | | | |
|---|---|---|---|
| 1261630 | 10/1986 | U.S.S.R. | 128/775 |

*Primary Examiner*—William E. Kamm
*Assistant Examiner*—Kennedy J. Schaetzle
*Attorney, Agent, or Firm*—Lewis Anten, Esq.; Amedeo Ferraro, Esq.

[57] ABSTRACT

A method for the diagnosis of preterm labor, and in particular for distinguishing between false labor and true labor, which includes both prelabor and active labor, is disclosed. The onset of a contraction is determined and the change in value of the rapid ejection time (RET) is determined from the onset of the contraction to a point of time just below the peak intensity of the contraction. A level value of the RET as the contraction proceeds is indicative of false preterm labor. An increasing value of the RET is indicative of prelabor. A decreasing value of the RET is indicative of active labor. The cutaneous blood pressure pattern (cPP) of the patient, which should be concordant with the slope of the RET, can be used as a check on the reliability of the apparatus.

18 Claims, 4 Drawing Sheets

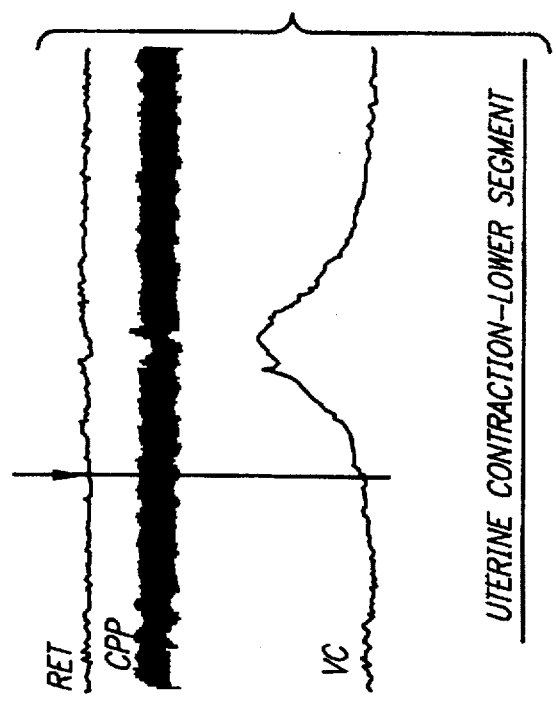
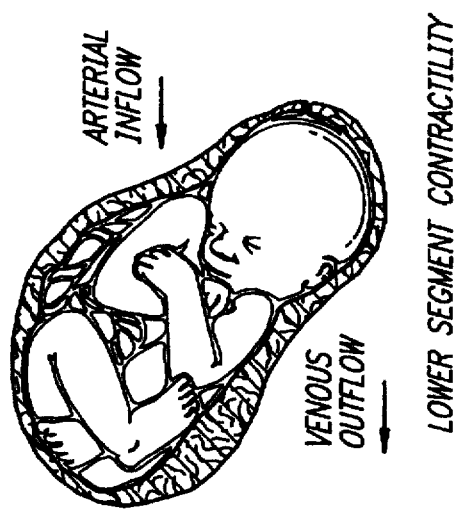
FIG. 1C
FIG. 1B
FIG. 1A

PRELABOR

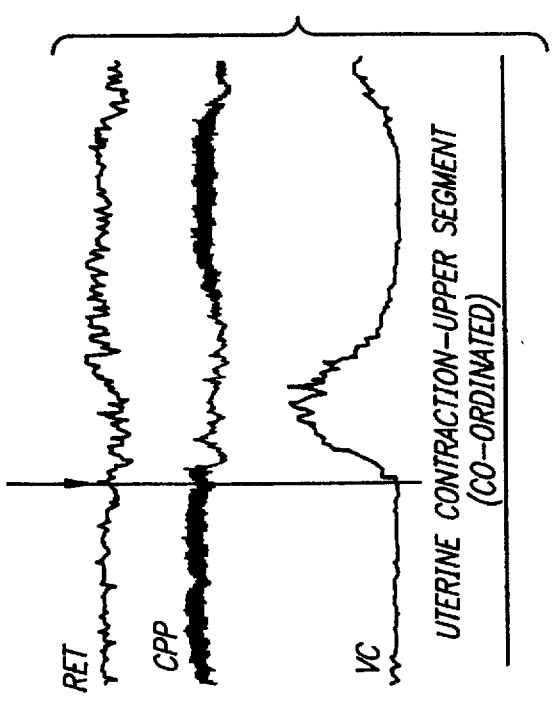
FIG. 3C
FIG. 3B
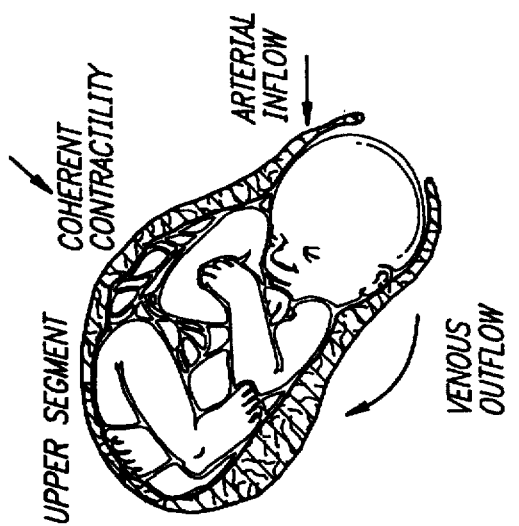
FIG. 3A

METHOD FOR THE DIAGNOSIS OF PRETERM BIRTH

RELATED APPLICATIONS

This is a continuation in part of patent application Ser. No. 08/085,547 entitled APPARATUS AND METHOD FOR NONINVASIVE MEASUREMENT OF PERIPHERAL PRESSURE PULSE COMPLIANCE AND SYSTOLIC TIME INTERVALS, filed on Jun. 30, 1993, now U.S. Pat. No. 5,497,778.

BACKGROUND

1. Field of the Invention

This invention relates to preterm birth, and more particularly to a method and apparatus for the diagnosis of preterm birth, and in particular for method and apparatus for distinguishing between false labor and true labor.

2. Description of the Related Art

Preterm birth is a major health problem and is currently the greatest cause of neonatal mortality and morbidity. The latter includes, not only the immediate cardiorespiratory problems of the small infant, but developmental deficits which have lifelong sequelae and handicaps. Despite numerous research and clinical obstetrical studies costing countless millions of dollars, little progress has been made in the diagnosis and management of this obstetrical problem. The medical gains that have been made are in the area of improved neonatal care which have resulted in reduced infant mortality and morbidity.

The paramount problem of a definitive diagnosis for preterm labor as basis for neonatal management, remains unresolved. As a consequence, there are confusing clinical definitions for preterm labor as well as confusing management regimens. Diagnosis is presently made by recording a given number of uterine contractions per 20 minute interval typically 4–6, obtained with a pressure sensing device held against the maternal abdominal wall with a belt or adhesive. This device is called a tocodynamometer or tocotransducer.

In addition to counting the number of uterine contractions which occur in a given period of time, some investigators require that there be some evidence of cervical softening and dilatation before "a diagnosis of preterm labor" can be made. Unfortunately, there is no uniform agreement as to the degree of cervical change that is required to qualify as an adjunct for this diagnosis. Hence there is no means of comparing results from different institutions.

Furthermore, the recording of uterine activity with a tocodynamometer is dependent, to a large extent, on the sensitivity of the instrument, the elastic property of the belt and the location of the tocotransducer. Another important factor is the size of the pregnant uterus relative to the thickness of the maternal abdominal wall. In an obese patient it may be difficult to record uterine contractions with a tocotransducer even though they are felt by the patient. This is especially true when the gestation is less than 30 weeks in duration.

It is clear from the foregoing that methodologic inadequacy is a prime factor in the diagnosis of preterm labor and consequent lack of definitive therapy.

SUMMARY OF THE INVENTION

The apparatus and method described in this patent application has been devised to concomitantly record detailed cardiovascular system changes associated with uterine contractions. A number of investigations have shown that with coordinated changes associated with uterine contractions there are marked changes in the uteroplacental circulation, varying from partial interruption to total cut-off of blood flow to the placenta. This modulation of placental blood flow is due to the anatomic relationship that exists between myometrial cells and the arteries and veins in the upper segment of the uterus whose co-ordinated muscular contractility provides the mechanical forces necessary to expel the fetus. In this segment of the uterus the myometrial cells form an interlacing network of muscle fibers so that the interlacing of any two gives approximately the form of the figure eight. When the cells contract they act as ligatures and constrict the blood vessels.

From the functional standpoint the uterus is two organs. The upper segment which is almost totally muscular has the primary function of providing expulsive forces. The lower segment which is primarily fibrous (contains about 10–25 percent muscle cells) functions as a means of retaining the uterine contents (fetus, amniotic sac and placenta). The disposition of the muscle cells in this passive lower segment are not intertwined as they are in the upper segment, but overlap one another like shingles on a roof. Hence myometrial activity in the lower segment of the uterus (which accompanies fibrous and collagenous cellular changes during cervical preparation for delivery) are not associated with hemodynamic changes of the magnitude seen with upper segment myometrial activity. From the clinical standpoint it is therefore, important to distinguish between activity in the upper uterine segment (expulsive force) activity from the lower uterine segment (preparatory cervical dilation). The former indicates that forces are in motion capable of expelling the fetus, while the latter reflects preparatory non-muscular tissue changes that may precede delivery by many weeks. The observation that about 60 percent of preterm labor (diagnosis based on the frequency of uterine contractions) do not lead to preterm delivery supports the clinical need to differentiate upper segment uterine activity from lower segment uterine activity. This cannot be done with a tocotransducer alone.

The apparatus devised to accomplish this differentiation is based on the acquisition of electrocardiographic, cutaneous pressure pulse and uterine activity (tocodynamometric) data from the pregnant patient and timing the detailed hemodynamic patterns with the uterine activity recordings.

Physiologically, the uteroplacental circulation is a hemodynamic shunt paralleling the general circulation. In the absence of upper segment uterine muscle activity the shunt is passive so its vascular resistance is relatively stable. With upper segment myometrial activity, the blood vessels are compressed to varying degrees depending on the activity level of the intertwined muscle cells. As a result shunt vascular resistance is no longer stable but varies with the level of upper segment uterine activity. As a consequence arterial input and venous outflow of this shunt are modulated by the level of uterine activity. The resultant and detailed hemodynamic changes are detected by the apparatus.

While it is likely that some hemodynamic changes also occur with lower uterine segment activity, they appear to be minimal and if present do not provide hemodynamic patterns detectable with the said apparatus.

OBJECTS OF THE PRESENT INVENTION

It is an object of the present invention to provide means for distinguishing false (preterm) labor from true labor.

It is another object of the present invention to provide a system of recording and comparing hemodynamic changes during contractions.

It is a further object of the present invention to provide a means of determining proper treatment of a patient based on whether there is false or true labor.

These and other objects of the present invention will become apparent from a review of the accompanying drawings and the detailed description of the drawings.

BRIEF DESCRIPTION OF THE DRAWINGS

FIG. 1A is a diagrammatic representation, with the fetus in the uterus, of a uterine contraction of the lower segment.

FIG. 1B is an illustration of a lower uterine segment uterine contraction recorded with a tocotransducer, concomitantly showing rapid ejection time (RET), the cutaneous blood pressure pulse (cPP), and the uterine contractions (UC).

FIG. 1C is a schematic diagram of the interplacental shunt illustrating the passive condition of the lower uterine contractility (false labor).

FIG. 3A is a diagrammatic representation, with the fetus in the uterus, of a coordinated uterine contraction of the upper uterine segment.

FIG. 3B is an illustration of an upper uterine segment coordinated uterine contraction recorded with a tocotransducer, concomitantly showing rapid ejection time (RAT), the cutaneous blood pressure pulse (cPP), and the uterine contractions (UC).

FIG. 3C is a schematic diagram of the shunt during a coordinated contraction of the upper uterine segment.

DETAILED DESCRIPTION OF THE DRAWINGS

Figure 2C:
FIG. 2C is a diagrammatic representation of the shunt during incoordinated uterine contraction of the upper segment.

The abbreviations used in this application are as follows: RET=rapid ejection time, cPP=cutaneous pressure pulse, and UC=uterine contraction.

The RET and cPP waves are obtained in the manner discussed in patent application Ser. No. 08/085,547 entitled APPARATUS AND METHOD FOR NONINVASIVE MEASUREMENT OF PERIPHERAL PRESSURE PULSE COMPLIANCE AND SYSTOLIC TIME INTERVALS, filed on Jun. 30, 1993, now U.S. Pat. No. 5,497,778 which is incorporated herein by reference.

The cutaneous blood pressure pulse (cPP) is acquired from the finger tip with a simple to use pressure transducer, instead of from the carotid artery pulse. The fingertip pressure transducer is disclosed in U.S. Pat. No. 4,993,422, issued Feb. 19, 1991 to Hon et al. and is incorporated herein by reference. The configuration of these cutaneous pressure pulses is similar to those obtained from the carotid artery and provides the basis for the development of peripheral systolic time interval measurements.

The systolic time intervals are used in cardiology are composed of two intervals:

1. Pre-ejection period (PEP): composed of the QRS depolarization time plus isovolumic contraction time (ICT), i.e., the interval from mitral valve closure (MC) to aortic valve opening (Ao).

2. Left ventricular ejection time (LVET); interval from the foot of the pulse to the incisura, i.e. from aortic valve opening (Ao) to closure (Ac).

The interval can be further subdivided into a rapid ejection phase to peak pulse pressure; and a reduced ejection phase (from the peak of the pulse to incusura).

In the textbook discussions of systolic time intervals, an aortic or carotid artery pulse has been used for measuring the various intervals. When the intervals are computed from a peripheral pulse instead of an aortic or carotid pulse, the following differences should be noted: The electromechanical interval (EMI) in the peripheral system is measured from the peak of the R-wave of the electrocardiogram (ECG) to the onset of the peripheral pulse; this interval is analogous to the ICT. In addition to this interval, EMI includes the pulse wave travelling time (PWTT). These two intervals, ICT and PWTT, together make up the pulse wave arrival time (PWAT). PWAT differs from PEP since it includes PWTT but omits QRS depolarization time. PEP omits PWTT, since systolic time intervals are derived from a central pulse. LVET in the peripheral systolic time interval system is analogous to that of the central system. We are also measuring the analog of the duration of the rapid ejection phase of the aortic pressure pulse and labeling it "rapid ejection time" (RET).

In the event that the heart rate and PWAT are desired to be used, they are available from the above apparatus and methodology. However, in the preferred embodiment of the present invention the cPP and the RET are all that are necessary for practice of the present invention, thereby avoiding using the electrocardiogram equipment and electrodes.

The data acquisition, processing and display systems have been described in detail previously. Briefly, the cutaneous pressure pulse transducer is applied over the distal phalanx of a finger of one hand ECG electrodes are attached to another finger or to the suprasternal area. The cPP transducer and ECG electrodes are plugged into a data processing unit connected to a laptop computer and a printer.

PWAT and RET Computations

A special microcomputer running at 11 MHz concurrently computes PWAT and RET. Data sampling is done at a rate of 2 milliseconds (mS) and the analog-to-digital conversion uses a 12-bit resolution. The ECG R-wave is located with a peak detector algorithm and the elapsed time from this point to the slope upturn of the cPP is determined. This interval is the PWAT. The RET is computed from the onset of the cPP slope upturn (the end-point of PWAT) to the peak of the cPP pulse.

A vertical line has been placed at the beginning of each uterine contraction as a reference point from which to compare the respective hemodynamic patterns associated with each type of uterine contraction. Attention is directed primarily to those patterns which occur with the uterine contraction since they serve as identification markers. Since RET is an indicator of vascular compliance it is modulated as the myometrial cells contract and relax. In these illustrations a decrease in compliance i.e. an increase in vascular resistance is depicted as an upward movement in RET. In the preferred embodiment the value of the RET is compared from the onset of the contraction, as indicted by an arrow or the vertical reference line in FIG. 1B, 2B, and 3B, to just below about 90% of the value of the peak intensity of the contraction. This is sufficient time to distinguish the absolute trend of the slope of the RET. The is also true of the slope or trend of the cPP which is concordant with the RET slope.

The use of the cPP serves as a check on the trend of the RET. While the cPP pattern is generally concordant with the RET, there may be momentary deviations in cPP from its general pattern since it responds more acutely to sympathetic stimuli than the RET. Accordingly, the RET is used as the primary indicator of the physiologic background of contractions and their clinical significance. While it is not the preferred embodiment of the present invention, it is possible to use the pattern of the cPP in place of the RET and to use the RET to check on the reliability of the cPP.

In FIG. 1B, as the uterine contraction begins, at the vertical reference line, the RET shows only minor changes. The slope of the RET is substantially level or constant. The value of the RET does not substantially change. This is also true during, preceding and following the contraction. This is expected since the myometrial cells of the lower segment are not entwined around vascular channels.

Figure 2B:
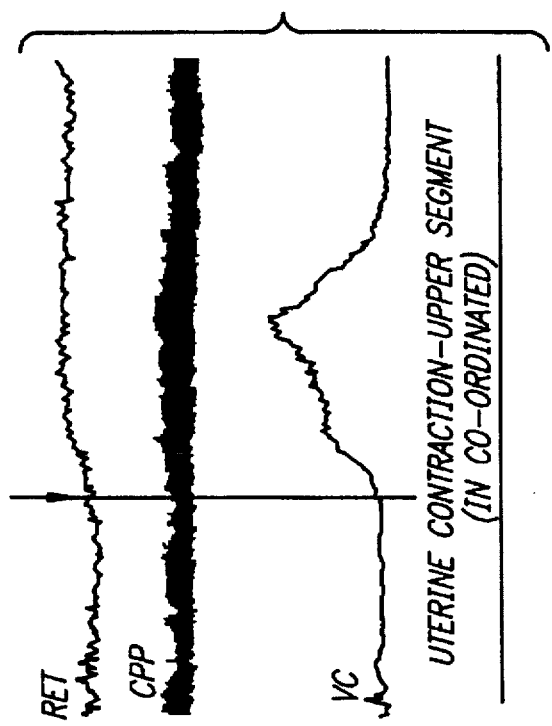
FIG. 2B is an illustration of an upper uterine segment incoordinated uterine contraction recorded with a tocotransducer, concomitantly showing rapid ejection time (RET), the cutaneous blood pressure pulse (cPP), and the uterine contraction (UC).

FIG. 2B is an illustration of the hemodynamic patterns associated with a uterine contraction of the upper uterine segment. Here the contraction activity of the myometrial cells is incoordinate (incoherent). However, those that are contracting cause an increase in vascular resistance which, at the vertical reference line shown as a positive slope or increasing value of the RET which flattens out as the uterine contraction approaches its peak. Note the downward slope in RET and its nadir immediately before the reference line. The concomitant cPP pattern associated with this RET pattern shows a similar slope on its upper boundary (systolic pressure).

FIG. 3B is an illustration of the hemodynamic patterns associated with an upper segment uterine contraction where the myometrial cells are contracting coordinately (coherent). Since the individual muscle cells are entwined around blood vessels the hemodynamic changes are more marked than those of FIG. 2B. In this situation, at the vertical reference point the RET slope is just slightly negative and then turns positive after the contraction's peak is reached. Initially is has an overall decreasing value or negative slope. As labor progresses the RET change becomes more marked. Note the marked narrowing of the cutaneous pressure pulse pattern and its negative slope.

It is clear that these three types of uterine contractions can be differentiated from one another by their hemodynamic concomitants. Their clinical implications are as follows:

FIG. 1A—This uterine contraction which has minimal discernible hemodynamic concomitants is considered as false preterm labor. Pregnancy may continue without interruption for weeks and months and no specific treatment is necessary. Unfortunately, clinically this tocodynamometer record cannot be differentiated from "prelabor" and "active labor" and consequently is frequently treated intensively. The result is unnecessary financial cost and increased neonatal morbidity and mortality caused by untimely interruption of pregnancy.

Figure 2A:
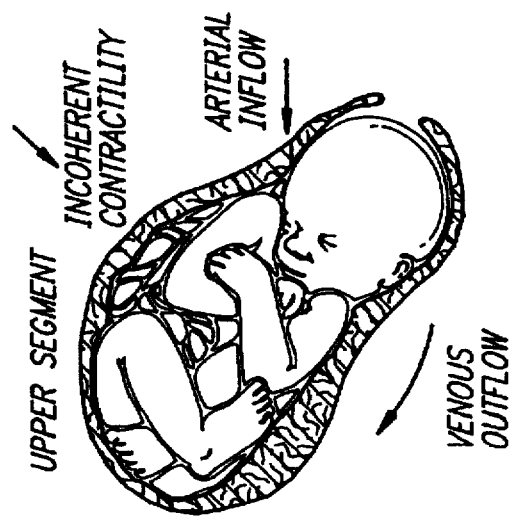
FIG. 2A is a diagrammatic representation, with the fetus in the uterus, of an incoordinated uterine contraction of the upper segment.
Figure 4:
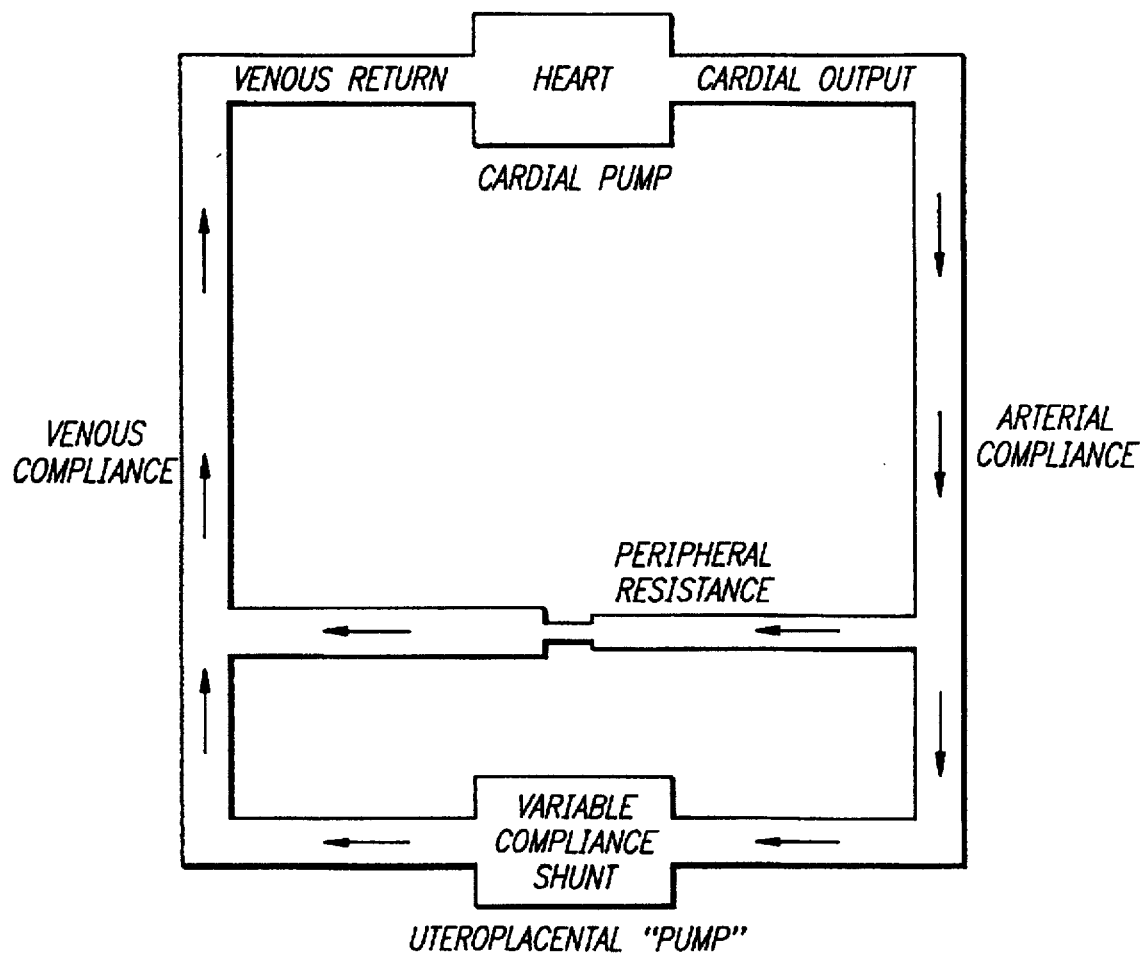
FIG. 4 is a schematic diagram of the maternal cardiovascular system showing the addition of a variable compliance vascular uteroplacental shunt whose compliance is subject to change by uterine activity.

FIG. 2A—This "prelabor" contraction has specific hemodynamic markers which clearly differentiate it from false labor. If it is not expedient to deliver the fetus in the immediate future. The patient must be treated to suppress the myometrial activity.

FIG. 3A—This type of uterine contraction with its associated hemodynamic markers is indicative of active labor. In this situation, delivery is expected within a few hours and suppression of uterine activity is extremely difficult (if it is desirable).

The foregoing demonstrates the ability of the apparatus to differentiate between clinically important uterine activity patterns whereas the tocodynamometer cannot. The information provided by this device provides a rational basis for medical treatment and consequently less neonatal morbidity and mortality.

While the present invention has been described in detail with regards to the preferred embodiment, it is appreciated that other variations of the present invention may be devised which do not depart from the inventive concept of the present invention.

What is claimed is:

1. A method for distinguishing false preterm labor from true labor (prelabor or active labor), comprising the steps of:
   a. obtaining a rapid ejection time (RET) pattern of a patient;
   b. determining the onset of a maternal contraction and the peak of the contraction of the patient;
   c. determining whether the rapid ejection time (RET) pattern from the onset of the contraction towards the peak of the contraction is remaining the same, increasing or decreasing; and
   d. diagnosing the type of labor of the patient.

2. The method of claim 1 including the step of diagnosing false preterm labor when the rapid ejection time (RET) pattern from the onset of the contraction toward the peak of the contraction is substantially constant.

3. The method of claim 1 including the step of diagnosing prelabor when the rapid ejection time (RET) pattern from the outset of the contraction toward the peak of the contraction is increasing.

4. The method of claim 1 including the step of diagnosing active labor when the rapid ejection time (RET) pattern from the onset of the contraction towards the peak of the contraction is decreasing.

5. The method of claim 1 including the step of measuring the rapid ejection time (RET) pattern from the onset of the contraction to 90% of the peak of the contraction.

6. The method of claim 1 including the additional steps of determining a cutaneous pulse pattern (cPP) of the patient; determining whether the cPP slope from the onset of the contraction towards the peak of the contraction is decreasing; and diagnosing active labor when the cPP slope is decreasing.

7. The method of claim 1 including the additional steps of determining the cutaneous pulse pattern (cPP) of the patient; determining whether the cPP slope from the onset of the contraction towards the peak of the contraction is increasing; and diagnosing prelabor when the cPP slope is increasing.

8. The method of claim 1 including the additional steps of determining the cutaneous pulse pattern (cPP) of the patient; determining whether the cPP slope from the onset of the contraction towards the peak of the contraction is relatively unchanged; and diagnosing false labor when the cPP slope is relatively unchanged.

9. The method of claim 1 including the step of diagnosing prelabor when the rapid ejection time (RET) pattern has a positive slope and increasing amplitude from the onset of the contraction toward the peak of the contraction.

10. The method of claim 1 including the step of diagnosing active labor when the rapid ejection time (RET) pattern falls shortly after the onset of the contraction and has a nadir coincident with the peak of the contraction.

11. A method for distinguishing false preterm labor from prelabor, comprising the steps of:

a. obtaining a rapid ejection time (RET) pattern of a patient;

b. determining the onset of a maternal contraction and the peak of contraction of the patient;

c. determining whether the rapid ejection time (RET) pattern from the onset of the contraction towards the peak of the contraction has a positive slope; and d. diagnosing prelabor.

12. The method of claim 11 including the step of diagnosing active labor when the rapid ejection time (RET) pattern has a negative slope from the onset of the contraction toward the peak of the contraction.

13. The method of claim 11 including the step of diagnosing false preterm labor when the rapid ejection time (RET) pattern has a substantially level slope.

14. A method for distinguishing false preterm labor from prelabor or active labor, comprising the steps of:

a. obtaining the cutaneous pulse pattern (cPP) of the patient;

b. determining the onset of maternal contraction and the peak of the contraction of the patient;

c. determining whether the slope of the cutaneous pulse pattern (cPP) from the onset of the contraction towards the peak of the contraction is remaining the same, increasing or decreasing; and d. diagnosing the type of labor of the patient.

15. The method of claim 14 including the step of diagnosing active labor when the slope of the cutaneous pulse pattern (cPP) from the onset of the contraction towards the peak of the contraction is decreasing.

16. The method of claim 14 including the step of diagnosing false preterm labor when the slope of the cutaneous pulse pattern (cPP) from the onset of the contraction towards the peak of the contraction is substantially constant.

17. The method of claim 14 including the step of measuring the cutaneous pulse pattern (cPP) from the onset of the contraction to the peak of the contraction.

18. The method of claim 14 including the additional step of determining the rapid ejection time (RET) pattern of the patient; determining whether the RET pattern from the onset of the contraction towards the peak of the contraction is decreasing; and diagnosing active labor when the RET pattern is decreasing.

* * * * *